United States Patent
Kim et al.

(10) Patent No.: US 10,500,393 B2
(45) Date of Patent: Dec. 10, 2019

(54) LIQUID CRYSTAL POLYMER-BASED ELECTRODE ARRAY AND PACKAGE FOR NEURAL IMPLANT, AND MANUFACTURING METHOD THEREFOR

(71) Applicants: SEOUL NATIONAL UNIVERSITY R&DB FOUNDATION, Seoul (KR); TODOC CO., LTD., Seoul (KR)

(72) Inventors: Sung June Kim, Seoul (KR); Jin Ho Kim, Seoul (KR); Kyou Sik Min, Seoul (KR); Jeong Hoan Park, Seoul (KR); Sung Eun Lee, Seoul (KR); Joon Soo Jeong, Seoul (KR)

(73) Assignees: SEOUL NATIONAL UNIVERSITY R&DB FOUNDATION, Seoul (KR); TODOC CO., LTD., Seoul (KR)

(*) Notice: Subject to any disclaimer, the term of this patent is extended or adjusted under 35 U.S.C. 154(b) by 221 days.

(21) Appl. No.: 15/502,083

(22) PCT Filed: Aug. 10, 2015

(86) PCT No.: PCT/KR2015/008344
§ 371 (c)(1),
(2) Date: Feb. 6, 2017

(87) PCT Pub. No.: WO2016/022003
PCT Pub. Date: Feb. 11, 2016

(65) Prior Publication Data
US 2017/0232250 A1    Aug. 17, 2017

(30) Foreign Application Priority Data
Aug. 8, 2014    (KR) .................. 10-2014-0102106

(51) Int. Cl.
*A61N 1/05*    (2006.01)
*A61F 2/14*    (2006.01)
(Continued)

(52) U.S. Cl.
CPC .............. *A61N 1/0543* (2013.01); *A61B 5/04* (2013.01); *A61B 5/04001* (2013.01);
(Continued)

(58) Field of Classification Search
None
See application file for complete search history.

(56) References Cited

U.S. PATENT DOCUMENTS

| 6,734,419 B1 * | 5/2004 | Glenn | H04N 5/2253 174/536 |
| 8,838,256 B2 * | 9/2014 | Mashiach | A61N 1/0558 607/134 |

(Continued)

FOREIGN PATENT DOCUMENTS

| KR | 10-2009-0108373 A | 10/2009 |
| KR | 10-1088806 B1 | 12/2011 |

(Continued)

OTHER PUBLICATIONS

International Search Report dated Nov. 24, 2015, issued to International Application No. PCT/KR2015/008344.

(Continued)

*Primary Examiner* — Allan W. Olsen
(74) *Attorney, Agent, or Firm* — Stein IP, LLC

(57) ABSTRACT

A method for manufacturing a liquid crystal polymer-based electrode array for a neural implant, according to the present invention, can comprise the steps of: forming a seed layer on a liquid crystal polymer substrate; forming a plating mold having a pattern selectively exposing a part of the upper part of the seed layer; plating an electrode material on the exposed seed layer by using the plating mold as a plating barrier layer; forming an electrode by removing the plating mold and the seed layer therebelow; embedding the electrode by compressing a liquid crystal polymer cover layer on (Continued)

the electrode; and forming an electrode site exposing the upper part of the electrode by selectively removing a part of the liquid crystal polymer cover layer.

7 Claims, 9 Drawing Sheets

(51) Int. Cl.
    *A61B 5/04*     (2006.01)
    *A61N 1/36*     (2006.01)
    *A61B 50/30*     (2016.01)
(52) U.S. Cl.
    CPC .......... *A61F 2/141* (2013.01); *A61N 1/36046* (2013.01); *A61B 2050/3015* (2016.02); *A61B 2562/125* (2013.01); *A61F 2240/001* (2013.01)

(56) References Cited

U.S. PATENT DOCUMENTS

| | | | | |
|---|---|---|---|---|
| 2003/0160314 A1* | 8/2003 | Crane, Jr. | ............ | G02B 6/4292 257/680 |
| 2003/0162319 A1* | 8/2003 | Crane, Jr. | ............ | H01L 23/055 438/106 |
| 2004/0012083 A1* | 1/2004 | Farrell | ............ | H01L 21/50 257/704 |
| 2004/0258885 A1* | 12/2004 | Kreutter | ............ | B01L 3/502707 428/156 |
| 2010/0253361 A1* | 10/2010 | Nakamura | ............ | G01N 27/42 324/464 |
| 2011/0288615 A1* | 11/2011 | Armstrong | ............ | A61B 5/0031 607/59 |
| 2011/0313269 A1* | 12/2011 | Kim | ............ | A61B 5/04001 600/373 |
| 2013/0211516 A1* | 8/2013 | Blum | ............ | A61F 2/14 623/6.22 |
| 2013/0237906 A1* | 9/2013 | Park | ............ | A61N 1/0551 604/93.01 |
| 2014/0107542 A1* | 4/2014 | Schubert | ............ | A61H 23/02 601/46 |
| 2015/0009644 A1* | 1/2015 | Rendek, Jr. | ............ | H01L 24/83 361/767 |
| 2018/0124928 A1* | 5/2018 | Rathburn | ............ | H05K 3/4644 |
| 2018/0133457 A1* | 5/2018 | Yao | ............ | A61B 5/686 |
| 2018/0333571 A1* | 11/2018 | Pepin | ............ | A61N 1/0551 |

FOREIGN PATENT DOCUMENTS

| | | |
|---|---|---|
| KR | 10-1304338 B1 | 9/2013 |
| KR | 10-2014-0090609 A | 7/2014 |

OTHER PUBLICATIONS

Korean Office Action dated Jan. 7, 2016, issued to Korean Application No. 10-2014-0102106.
Kyou Sik Min, A Study on the Liquid Crystal Polymer-Based Intracochlear Electrode Array, Feb. 2014, Department of Electrical Engineering and Computer Science College of Engineering Seoul National University.

* cited by examiner

PRIOR ART

PRIOR ART

LIQUID CRYSTAL POLYMER-BASED ELECTRODE ARRAY AND PACKAGE FOR NEURAL IMPLANT, AND MANUFACTURING METHOD THEREFOR

CROSS-REFERENCE TO RELATED APPLICATIONS

This application is a national stage of International Application No. PCT/KR2015/008344, filed Aug. 10, 2015, which claims the benefit of priority to Korean Application No. 10-2014-0102106, filed Aug. 8, 2014, in the Korean Intellectual Property Office, the disclosures of which are incorporated herein in their entireties by reference.

TECHNICAL FIELD

The present invention relates to a liquid crystal polymer-based neural implant, and more particularly, to an electrode array and package for a liquid crystal polymer-based neural implant adequate for being applied to a liquid crystal polymer-based neural implant apparatus and a method of manufacturing the same.

BACKGROUND ART

As is well known, a neural implant includes a sealed package portion with an electronic component (or an electronic module) built therein and an electrode portion configured to interface with nervous tissue and input or output a signal to or from an electronic component. The electrode portion that interfaces with nerves generally has a multi-channel electrode site and interacts with a nerve cell or tissue to transfer electrostimulation or to measure various micro bio-signals caused by nervous tissue after being inserted into a human body.

In the case of a conventional neural implant, an electrode is manufactured based on a micro metal (for example, Pt:Ir (90:10) alloy and the like) wire and a sealed package is realized using a titanium package, a ceramic insulator, and a platinum feedthrough.

However, since such conventional neural implants are manually manufactured and need a high skill level in manufacturing an electrode and a complicated packaging process, manufacturing costs increase and a yield is low.

To overcome such limitations, a liquid crystal polymer-based neural implant in which a multi-channel electrode portion is manufactured using a semiconductor process and a sealed package is realized using only a simple thermocompression process has been provided. Since a liquid crystal polymer has water permeability and gas permeability significantly lower than those of existing biocompatible polymers such as polyimide, parylene-C and the like, a lifespan of a polymer-based neural implant may be greatly increased.

FIGS. 1a to 1d are process flow diagrams illustrating main processes of manufacturing a liquid crystal polymer-based neural electrode according to a conventional method.

Referring to FIG. 1a, an electrode material 104a is having a thickness of several hundred nm is stacked on a high temperature liquid crystal polymer substrate 102 (with a melting point of 310 degrees) by performing an evaporation or sputtering process.

Subsequently, a photoresist material is applied thereto and a photolithography process and the like are performed, thereby forming, for example, a photoresist pattern 106 having an arbitrary pattern on the electrode material 104a as shown in FIG. 1b.

Next, an etching process (for example, a wet etching process) with the photoresist pattern 106 as an etching barrier layer is performed and then a residual photoresist pattern is removed (stripped), thereby forming, for example, an electrode 104 having an arbitrary pattern as shown in FIG. 1c.

Afterward, since a thermocompression process is performed using a heating press and the like, for example, as shown in FIG. 1d, a liquid crystal polymer cover layer with a site window 108 formed therein is adhered to a front surface of the liquid crystal polymer substrate 102 with the electrode 104 formed therein. Here, the site window 108 that exposes a top of the electrode 104 may be defined as an electrode site.

However, in a conventional method of manufacturing a micro neural electrode, when high pressure is applied during a thermocompression process for combining a liquid crystal polymer cover layer, for example, disconnection in which a metal pattern (a lead wire) breaks due to a thin conductor as shown as 202 in FIG. 2 occurs. To prevent such disconnection, it may be considered to lower thermocompression pressure. However, in this case, since adequate pressure is not transferred between a liquid crystal polymer substrate and a cover layer, adhesion between layers is decreased.

Also, in the case of a conventional micro neural electrode, an electrode site (a part in which a metal is exposed to interface with a nerve cell) at a liquid crystal polymer-based electrode is formed by making a hole corresponding to a site window at a liquid crystal polymer cover layer using a laser in advance and a liquid crystal polymer substrate and a cover layer are aligned and stacked using a metal pin and then adhered through thermocompression. In this case, for example, as shown in FIG. 3, the hole made in advance may become narrower or blocked as the cover layer is melted during the thermocompression process.

Additionally, in the conventional method of manufacturing a micro neural electrode, the minimum thickness of a liquid crystal polymer film in commercial use is limited to 25 μm and the minimum thickness of an electrode manufacturable when a substrate and a cover layer are thermally compressed is limited to 50 μm. Due to the limitations of thickness, it is difficult to realize an electrode with high flexibility (for example, an electrode that is inserted into a retina).

Also, since a liquid crystal polymer film having a thickness of several tens of μm has inferior optical characteristics (for example, permeability and the like), it is impossible to integrate an optical sensor that needs high resolution (a photodiode and the like) inside a sealed package.

Also, in the case of a liquid crystal polymer-based electrode, various processes are performed on a liquid crystal polymer film attached to a wafer and finally an outline is cut through laser cutting. For example, as shown in FIG. 4, due to an alignment error of laser equipment for laser cutting, a metal pattern of a lead wire (an internal connection line) 402 and the like may be cut out. In FIG. 4, 404, which is an unmentioned reference number, refers to an electrode site.

To prevent such problems, since it is necessary to cut with a margin at or above an alignment error, it is difficult to manufacture micro sized electrodes due to this.

Also, in the conventional method of manufacturing a micro neural electrode, since a liquid crystal polymer film is simply positioned above and below a circuit with an electronic component attached thereto and then thermocompression is performed while a sealed package portion is packaged, excessive pressure is applied to the electronic component in such a way that a risk of disconnection, short circuit, or a failure of the component may be present. Also, since uniform pressure is not transferred between liquid crystal polymer films, a crease and the like is generated in such a way that not only aesthetics may be spoiled but also sealability decreases. Such problems may become more severe in that case of a sealed package that needs a curved surface, for example, an artificial retina attachable to an eyeball.

DISCLOSURE OF INVENTION

Technical Problem

The present invention provides a detailed process technology and a sealed-packaging technology used in manufacturing a neural electrode using a liquid crystal polymer and a sealed package in manufacturing a neural implant device capable of not only manufacturing an electrode having a high yield in a semiconductor process and uniform characteristics but also being utilizable for various human body insertable devices by manufacturing an electrode portion and a sealed package portion, which are two parts of a neural implant, using a liquid crystal polymer that has excellent biocompatibility, water permeability, and gas permeability.

The aspects of the present invention are not limited to the above description, and additional aspects of the present disclosure will be set forth in part in the description which follows and will be obvious from the description to one of ordinary skill in the art.

Technical Solution

An aspect of the present invention provides a method of manufacturing an electrode array for a liquid crystal polymer (LCP)-based neural implant, including forming a seed layer on an LCP substrate, forming a plating mold having a pattern configured to selectively expose a part of a top of the seed layer, plating the exposed seed layer with an electrode material using the plating mold as a plating barrier layer, forming an electrode by removing the plating mold and the seed layer therebelow, embedding the electrode by compressing an LCP cover layer onto the electrode, and forming an electrode site that exposes a top of the electrode by selectively removing a part of the LCP cover layer.

The method may further include, before the forming of the electrode site, evenly removing the LCP substrate and the LCP cover layer to a certain thickness.

The removing of the LCP substrate and the LCP cover layer may be performed through a laser etching process.

The seed layer may be formed through an evaporation or sputtering process.

The plating mold may be a photoresist pattern.

The LCP cover layer may be a plasma-treated LCP.

The selectively removing of the part of the top of the LCP cover layer may be performed through a laser etching process.

Another aspect of the present invention provides an array and package for an LCP-based neural implant, including a sealed package portion with an electronic component embedded therein and an electrode portion with a multi-channel electrode site pattern electrically connected to the electronic component through a plurality of lead wires, Herein, the lead wires in the electrode portion are arranged inside the electrode portion and the multi-channel electrode site pattern is disposed outside the electrode portion.

Still another aspect of the present invention provides a method of manufacturing a package for an LCP-based neural implant, including mounting an electronic component at a certain position on an electronic board, manufacturing a component structure by stacking an intermediate substrate having a cavity that accommodates the electronic component on the electronic board, aligning the component structure at a certain position on an LCP substrate, and manufacturing a package by aligning and pressurizing an LCP cover layer on the component structure.

The method may further include, after the manufacturing of the component structure, filling the cavity with LCP powder.

The intermediate substrate may be formed of an LCP film in a multilayer structure.

The cavity may be formed through a laser etching process.

The method may further include, before the aligning of the LCP cover layer, forming an optical window at a certain position on the LCP cover layer.

The optical window may be formed through a selective pressurizing process using a mold having flatness.

The optical window may be formed through a laser etching process.

The optical window may be formed through a plasma etching process.

Yet another aspect of the present invention provides a method of manufacturing a package for an LCP-based neural implant, including mounting an electronic component on a curved type LCP substrate, filling a curved area with LCP powder to embed the electronic component, aligning a concave type LCP cover layer at a target position on the curved type LCP substrate, and manufacturing a curved type sealed package by pressurizing the curved type LCP substrate and the concave type LCP cover layer using a curved type lower press jig opposite to a curved surface and a concave type upper press jig opposite to a concave surface.

Advantageous Effects

In a liquid crystal polymer-based neural implant according to the present invention, since it is possible to manufacture an electrode using a semiconductor process and to manufacture a sealed package using thermocompression, compared with a conventional neural implant device based on a metal wire and a metal package, not only a yield can be relatively improved but also manufacturing costs can also be significantly lowered and it is possible to provide a relatively large number of channels in the same area.

BEST MODE FOR INVENTION

Figure 1A:
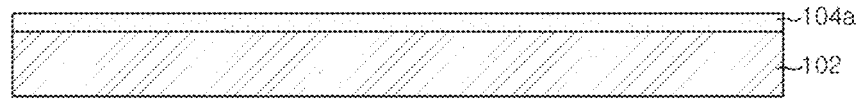
FIGS. 1*a* to 1*d* are process flow diagrams illustrating main processes of manufacturing a liquid crystal polymer-based neural electrode according to a conventional method.
Figure 1B:
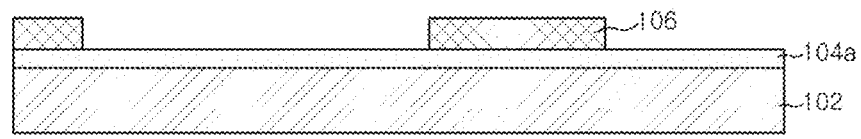
Figure 1C:
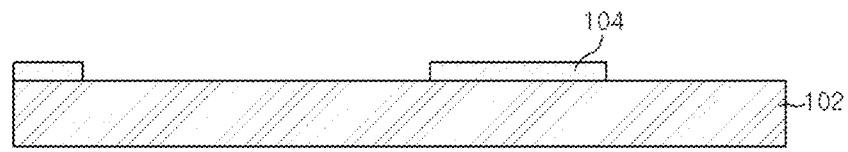
Figure 1D:
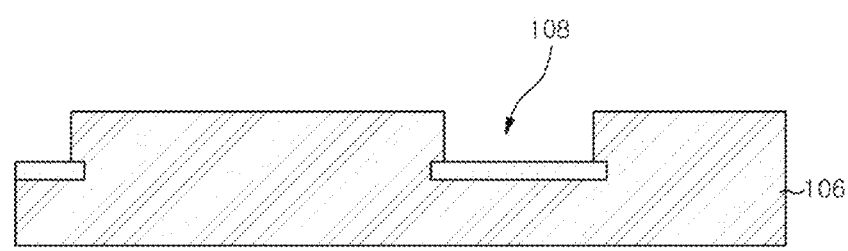
Figure 2:
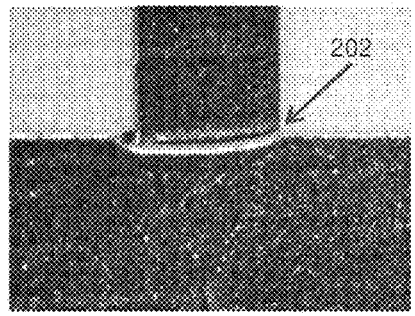
FIG. 2 is a photo illustrating a phenomenon in which a metal pattern breaks when a liquid crystal polymer is adhered using a thermocompression bonding process according to the conventional method.
Figure 3:
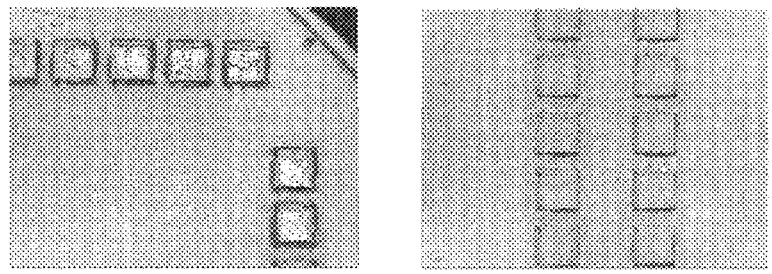
FIG. 3 is a photo illustrating a phenomenon in which an electrode site is partially or totally blocked when a liquid crystal polymer is adhered using a thermocompression bonding process according to the conventional method.
Figure 4:
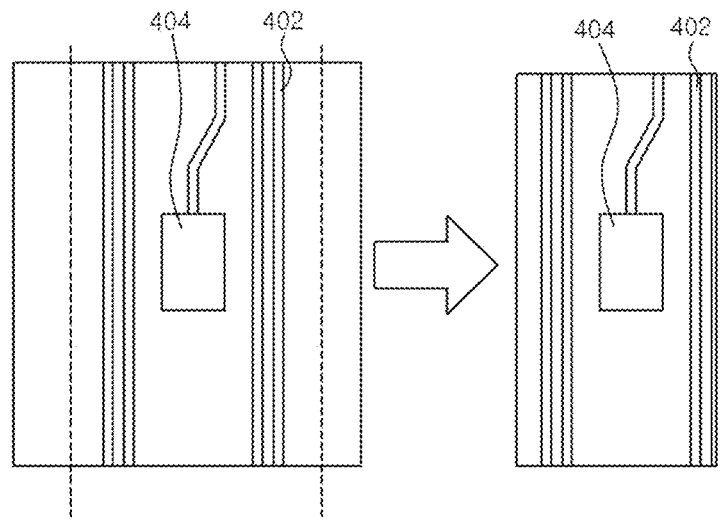
FIG. 4 is a view illustrating a phenomenon in which a lead wire is cut due to an error that occurs in laser cutting when a neural electrode is manufactured according to the conventional method.

First, advantages and features of the present invention and a method of achieving the same will become obvious by referring to the attached drawings and following embodiments described in detail. Here, the present invention is not limited to following embodiments and may be embodied in various different forms. However, since the embodiments are exemplarily provided to allow one of ordinary skill in the art to clearly understand the scope of the present invention, the technical scope of the present invention should be defined by the claims.

Additionally, in the following description of the present invention, certain detailed explanations of well-known functions or components of the related art will be omitted when it is deemed that they may unnecessarily obscure the essence of the present invention. Also, since the terms described below are defined considering functions thereof in the embodiments, they may vary with intentions of a user and an operator, practice or the like. Therefore, definitions thereof should be made based on the technical concept that will be described throughout the present specification.

First, a conventional liquid crystal polymer-based electrode portion may have problems such as a cut lead wire (a conducting wire), blockage of an electrode site, difficulty in controlling flexibility, a low yield caused by a laser cutting error and the like while being manufactured.

To solve the problems, according to the present invention, the problem in which the lead wire (the conducting wire) is cut while being manufactured may be overcome by forming a metal pattern having a thickness of several μm or more using a plating process using a plating mold (a photoresist pattern) of a thin film. Also, the problem in which the electrode site is blocked and which occurs while a precut liquid crystal polymer cover layer is thermally compressed may be solved by attaching a liquid crystal polymer film using thermocompression in advance and laser-etching a part corresponding to the electrode site using a separate align key.

Also, the problem in controlling the flexibility of an electrode may also be solved by adjusting a thickness of a polymer film by laser-etching a liquid crystal polymer cover layer or a liquid crystal polymer substrate to a target thickness after manufacturing the electrode. The problem in which the lead wire (the conducting wire) breaks due to an error of a laser alignment device and align key at a final laser cutting may be solved using an electrode design unsusceptible to a laser error in which the lead wire is disposed in a central part of an electrode portion and an electrode site pattern is disposed at an edge.

Also, there is provided a method of overcoming the difficulty in protecting an electronic component and a lead wire inside a flat type package in thermocompression for manufacturing a liquid crystal polymer-based sealed package portion, a crease generated due to unevenly transferred pressure in a flat type or curved type packaging process, and the occurrence of a defective package caused by the crease, and an undesirable optical characteristic problem caused by a thickness of a film.

That is, the problem in protecting the electronic component and the lead wire inside the flat type package may be solved by forming a recessed cavity in a liquid crystal polymer film corresponding to an intermediate substrate positioned between a liquid crystal polymer cover layer and a liquid crystal polymer substrate in advance using a laser cutting process and then disposing and packaging the same.

Also, in the flat type package, it is possible to transfer uniform pressure while packaging the components described above.

Also, the cavity may be filled with liquid crystal polymer powder and the like and then the liquid crystal polymer cover layer may be applied, thereby forming a smooth surface thereof.

Also, when there is an empty space while manufacturing a curved type package, a soft surface of a curved surface may be distorted due to expansion, contraction and the like of air. To solve this, the space of the curve is filled with liquid crystal polymer powder and packaged, thereby not only preventing a distortion but also better enduring external mechanical stress and preventing a failure of an electronic component caused by condensation upon moisture penetration.

In addition, the optical characteristic of a liquid crystal polymer-based sealed package may be generated by laser-etching, plasma-etching, or thermally compressing an area in which an optical sensor will be positioned or is positioned, about a melting point using a jig formed of a material having a flat surface such as silicon, glass and the like.

Hereinafter, exemplary embodiments of the present invention will be described in detail with reference to the attached drawings.

FIGS. 5a to 5g are process flow diagrams illustrating main processes of manufacturing an electrode array for a liquid crystal polymer-based neural implant according to embodiments of the present invention.

Figure 5A:
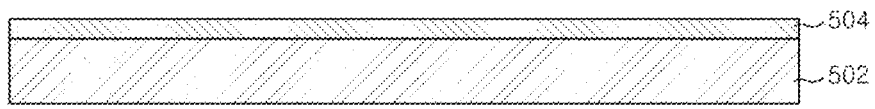
FIGS. 5a to 5g are process flow diagrams illustrating main processes of manufacturing an electrode array for a liquid crystal polymer-based neural implant according to embodiments of the present invention.

Referring to FIG. 5a, a seed layer having a thickness of several hundred nm, for example, a seed layer 504 such as Ti/Au and the like is formed on a liquid crystal polymer (LCP) substrate 502 that has been plasma-treated, by an evaporation or sputtering process. Here, the LCP substrate 502 may be defined as, for example, a base substrate and plasma treatment is performed on the surface to strengthen adhesion with a metal.

Figure 5B:
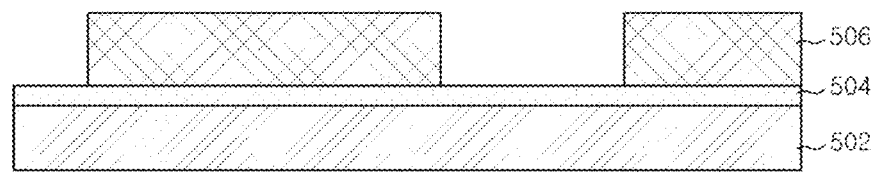

Next, the entire surface of the seed layer 504 is coated with a thick film photoresist having a thickness of several or several tens of m and then a photolithography process is performed, thereby forming, for example, a photoresist pattern having an arbitrary pattern, that is, a plating mold 506 having a thickness of several tens of μm on the seed layer 504 as shown in FIG. 5b.

Figure 5C:
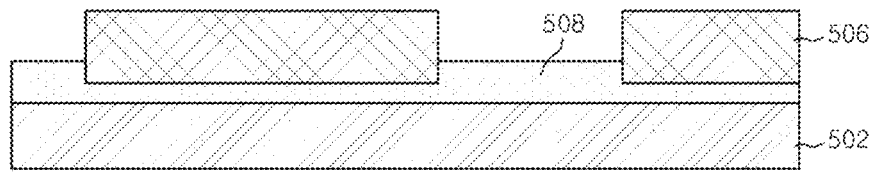

Subsequently, a plating process (for example, a wet etching process) with the plating mold 506 as a plating barrier layer is performed, thereby forming, for example, an electrode 508 by filling an empty space of the exposed seed layer 504, that is, the plating mold 506 with an electrode material (for example, Au, Pt and the like) having a thickness of several μm as shown in FIG. 5c.

Here, the relatively thick electrode 508 is formed by filling the empty space of the plating mold with the electrode material through a plating process using the plating mold 506 to suppress the disconnection of an electrode line and to strengthen adhesion between the electrode line and a LCP cover layer during a following thermocompression process, that is, thermally compressing the LCP cover layer onto the electrode with high pressure.

Figure 5D:
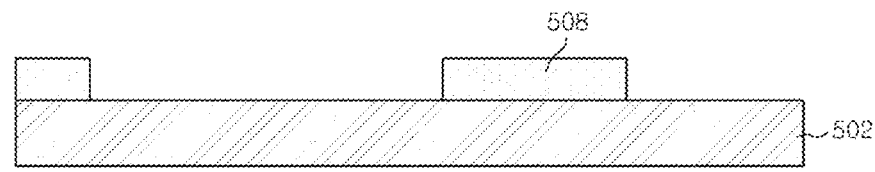

Afterward, the plating mold 506 that remains and the seed layer 504 formed therebelow are selectively removed, thereby completely forming, for example, the electrode 508 having an arbitrary pattern on the LCP substrate 502 as shown in FIG. 5d.

Figure 5E:
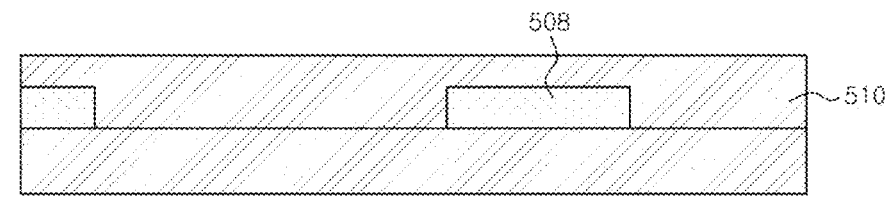

Once again, a lamination process is performed using a thermocompression process, a laser welding process or the like, thereby adhering, for example, an LCP cover layer 510 having a thickness about several tens of m on the entire surface of the LCP substrate 502 with the electrode 508 formed thereon as shown in FIG. 5e. Here, the minimum thickness of the LCP cover layer 510 is approximately 25 μm, and the minimum thickness of an electrode available when the base substrate and the LCP cover layer are combined may be approximately 50 μm.

Figure 5F:
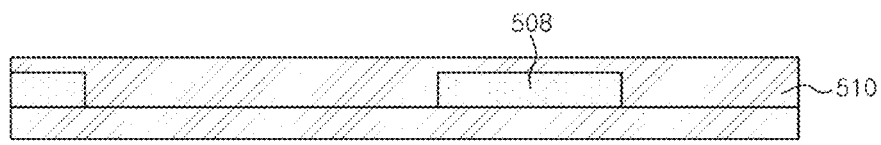

Meanwhile, in the method of manufacturing an electrode for an electrode array package according to the present invention, when an electrode needs flexibility, a laser etching process and the like is performed, thereby providing (realizing), for example, a relatively flexible electrode portion through evenly removing the LCP substrate 502 and the LCP cover layer 510 to a certain thickness as shown in FIG. 5f.

That is, in the present invention, thicknesses of a liquid crystal polymer substrate of an electrode portion generated through thermocompression and a liquid crystal polymer cover layer are adjusted using a laser etching process, thereby flexibly adapting a mechanical property of the electrode portion, for example, a bending property and the like.

Figure 5G:
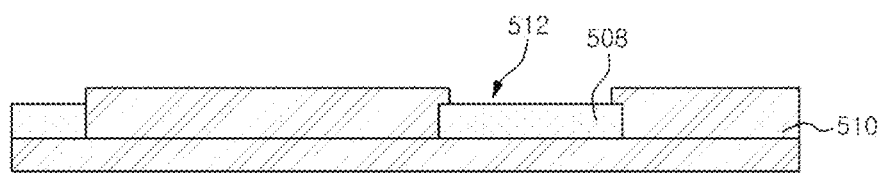

Afterward, a part of the LCP cover layer 510 is selectively removed through laser etching using a separate align key, thereby forming, for example, an electrode site (or a metal site) 512 that exposes a top of the electrode 508 as shown in FIG. 5g. Here, the electrode site 512 may be implanted around nerve cells or tissue and interface with an implant device to perform a function of collecting a neural signal and stimulating. Here, an electrode material may be embedded in the electrode site 512 through a sputtering or plating process.

Figure 6:
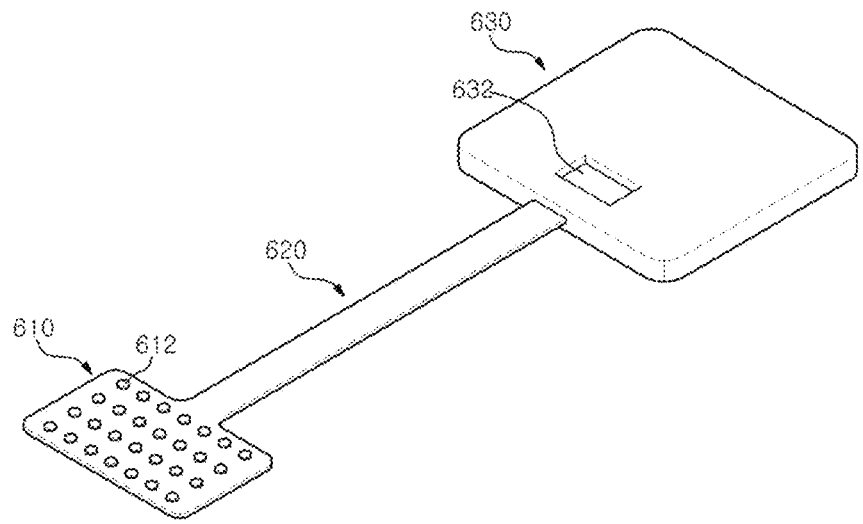
FIG. 6 is an exemplary structural drawing of an electrode array and package for a liquid crystal polymer-based neural implant manufactured according to embodiments of the present invention.

FIG. 6 is an exemplary structural drawing of an electrode array and package for a liquid crystal polymer-based neural implant manufactured according to embodiments of the present invention.

Referring to FIG. 6, the electrode array and package for a liquid crystal polymer-based neural implant may include an electrode portion 610 with a multi-channel electrode site 612 formed thereon, a lead wire pattern portion 620 in which a plurality of lead wires (not shown) are formed to connect the electrode portion 610 with a sealed package portion 630, and the sealed package portion 630 with an electronic component (not shown) mounted therein and with an optical window 632 formed on one outer side thereof.

Here, the electrode portion 610 refers to an electrode array for a neural implant according to the present invention described above with reference to FIG. 5 and may overcome a limitation of a conventional electrode forming process by forming (generating) a multi-channel electrode site through a laser etching process using a separate align key.

Figure 7:
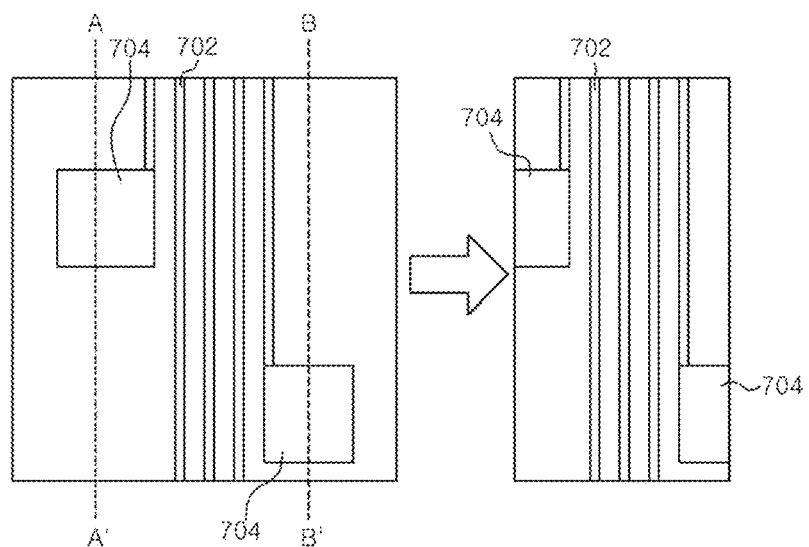
FIG. 7 is a view illustrating an arrangement structure for disposing a lead wire inside an electrode portion so as not to be cut due to an error that occurs in laser cutting when a neural electrode is manufactured according to embodiments of the present invention.

Also, in the case of an electrode portion according to the present invention, for example, as shown in FIG. 7, a metal pattern 702 of a lead wire (an internal connection line) and the like is disposed inside the electrode portion and a multi-channel electrode site pattern 704 having a relatively larger area is disposed outside the electrode portion, thereby preventing the metal pattern 702 from being cut due to an alignment error of laser equipment for an operation of cutting an outline of the electrode portion. Through this, it is possible not only to provide relatively high product reliability and product yield but also to manufacture a micro-sized electrode. In FIG. 7, line A-A' and line B-B' shown as dot lines indicate laser cutting lines.

That is, the electrode portion according to the present invention may have a structure in which each lead wire is disposed in (a central portion of) the electrode portion and the multi-channel electrode site pattern is disposed outside (at an edge of) the electrode portion. Through this, even though an error occurs during laser cutting, a lead wire is not cut and a part of an electrode site having a relatively larger size is cut.

Meanwhile, a process of manufacturing an electrode array for a neural implant according to the present invention may be performed on wafer units. Generally, one wafer includes several electrodes (an electrode portion) and such electrodes are separated into each electrode unit using a laser cutting process after the process is completed.

FIGS. 8a to 8e are process flow diagrams illustrating main processes of manufacturing a package for a liquid crystal polymer-based neural implant according to embodiments of the present invention.

Figure 8A:
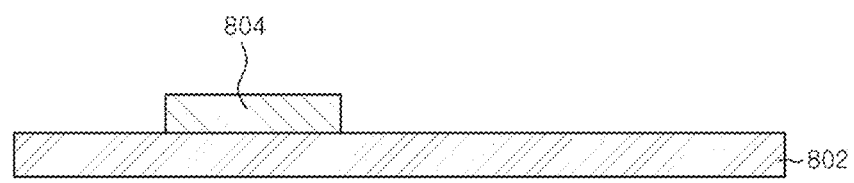
FIGS. 8a to 8e are process flow diagrams illustrating main processes of manufacturing a package for a liquid crystal polymer-based neural implant according to embodiments of the present invention.

Referring to FIG. 8a, at least one electronic component (or an electronic module) 804 is mounted at a certain position on an electronic board (or a circuit board) 802 by performing a component attaching process. Here, although not shown in the drawings, the electronic board 802 may refer to a circuit board having a structure in which an electronic component and an electrode portion are combined. When the electrode portion is separated, the electrode portion may be electrically connected as necessary when the electronic component and the like are assembled with the circuit board.

Figure 8B:
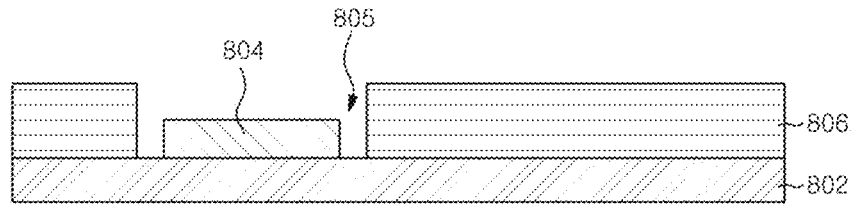

Next, an intermediate substrate 806 with a cavity 805 having a structure configured to accommodate the electronic component 804 mounted on the electronic board 802 is prepared and then stacked at a target position on the electronic board 802, thereby manufacturing, for example, a component structure as shown in FIG. 8*b*. Here, the intermediate substrate 806 may be, for example, an LCP film having a multilayer structure and the cavity 805 may have a height capable of adequately accommodating even an electronic component having a maximum height.

Also, the cavity 805 formed in the intermediate substrate 806 may be formed through, for example, a laser etching process.

Meanwhile, although not shown in FIG. 8, a method of manufacturing a package for a neural implant according to the present invention may further include a process of stacking the intermediate substrate 806 at a target position on the electronic board 802 and then filling the cavity 805 in which the electronic component 804 is accommodated with liquid crystal polymer powder. Through this, it is possible to suppress an external mechanical shock and an internal moisture condensation possibility after packaging. Here, the powder may be powder formed by mechanically grinding LCP pellets or film.

Particularly, the LCP powder filled in the cavity in which the electronic component is accommodated may have a greater effect when realizing a curved sealed package that is to be attached to the surface of living tissue such as an eyeball-attached artificial retina system.

Figure 8C:
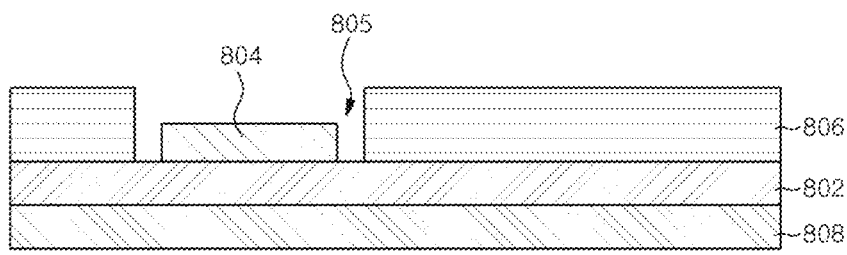

Referring to FIG. 8*c* again, the component structure in which the electronic component 804 and the intermediate substrate 806 are mounted and stacked on the electronic board 802 is aligned at a certain position of an LCP substrate 808.

Figure 8D:
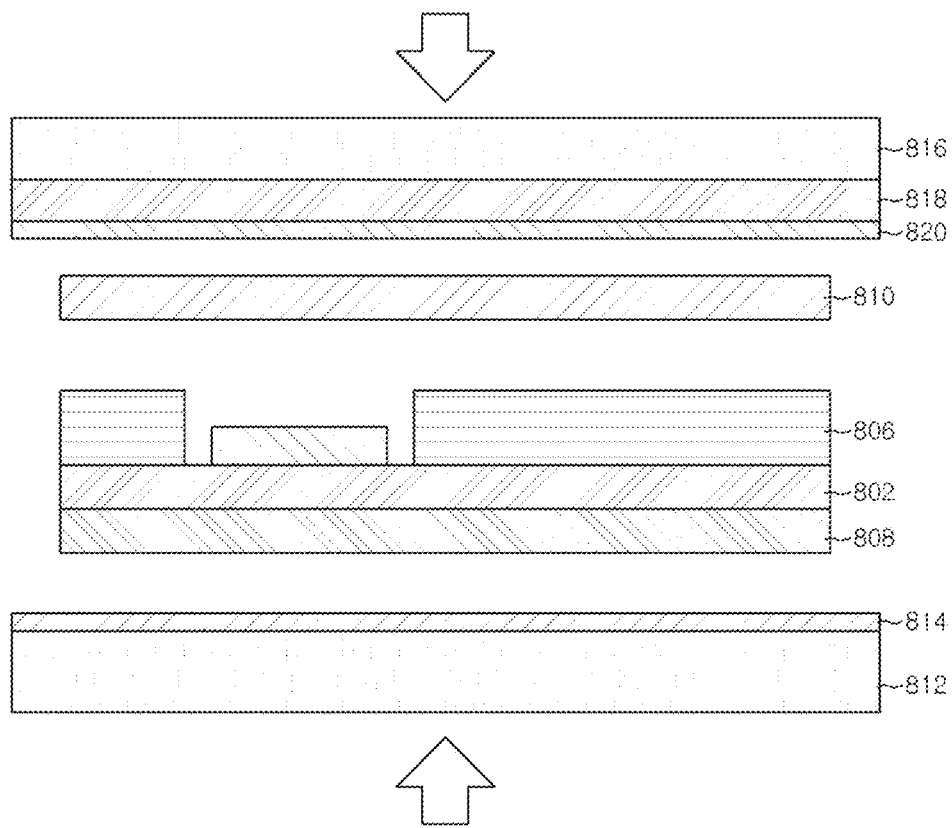
Figure 8E:
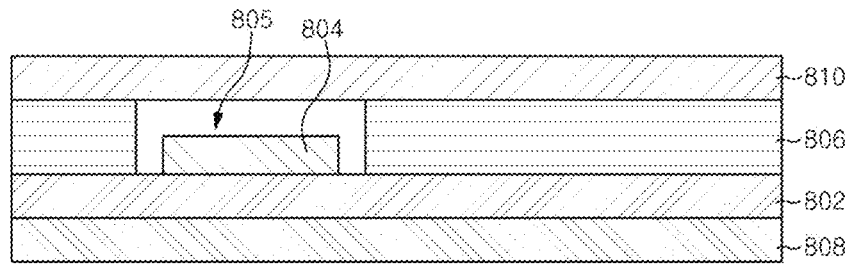

Subsequently, referring to FIG. 8*d*, an LCP cover layer 810 is positioned and aligned above the component structure, a lower metal plate 812 in contact with a bottom of the LCP substrate 808 and an upper metal plate 816 in contact with a top of the LCP cover layer 810 are pressurized (for example, a thermocompression process and a lamination process through laser welding and the like) in an arrow direction, and then the lower metal plate 812 and the upper metal plate 816 are detached, thereby manufacturing, for example, a package having a structure, that is, an LCP-based neutral implant package as shown in FIG. 8*e*.

Here, the lower and upper metal plates 812 and 816 have flatness, for example, a release layer 814 such as Teflon and the like may be formed on the lower metal plate 812 in contact with the LCP substrate 808, and a ceramic cushion layer 818 and a release layer 820 may be formed on the upper metal plate 816 in contact with the LCP cover layer 810.

Meanwhile, in the case of a neural implant that interfaces with an optical sensor (for example, a photodiode array), it is necessary to have an optical window (for example, 632 of FIG. 6) in a sealed package. In this case, an optical window may be formed by performing a laser thinning process or a plasma etching process on an LCP-based sealed package or may be formed using a method of thinning a thickness of an LCP cover layer by performing a thermocompression process at or above a melting point of an LCP using a mold (a pressurized mold) having flatness such as silicon, sapphire, glass and the like.

For example, in the case of an artificial retina system using an image sensor such as a photodiode and the like, it is necessary to integrate an optical sensor inside a sealed package. An optical window with high optical transparency is necessary for a part of a sealed package of a neural implant apparatus that needs such a property.

Here, using a material with excellent flatness for a thermocompression process for forming an optical window is intended to suppress a decrease in transmittance caused by scattering of light due to the occurrence of micro irregularities formed on the surface of a thin LCP film.

Also, an optical window may be generated through plasma etching. Even though the plasma etching has a longer process time than that of solution etching, the occurrence of the micro irregularities on the surface may be reduced, thereby suppressing the decrease in transmittance caused by scattering of light and the like.

Also, an optical window using laser etching may be formed using a method in which a part of the sealed package is partially etched by generating a grid pattern of laser beams and then repeatedly emitting laser beams. Here, it is necessary to optimize a laser parameter and pattern not to leave irregularities on the surface after etching.

Figure 9A:
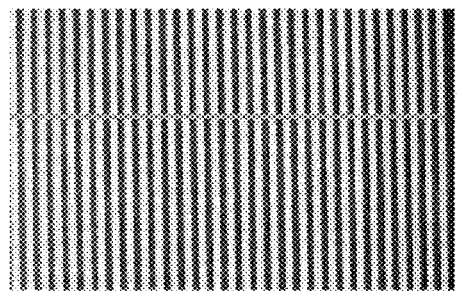
FIG. 9a is a view illustrating an image obtained by measuring a striped image pattern with 19 μm pitch by a complementary metal-oxide semiconductor (CMOS) image sensor without a liquid crystal polymer film.
Figure 9B:
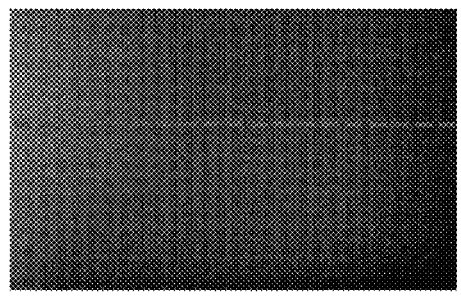
FIG. 9b is a view illustrating an image obtained by measuring after the same pattern as shown in FIG. 9a is attached to a CMOS image sensor of a 25 μm liquid crystal polymer film to which an optical window generation process is not applied.

FIGS. 9*a*, 9*b*, 9*c*, and 9*d* are views illustrating light transmittance degrees before and after generating an optical window. FIG. 9*a* is a view illustrating an image obtained by measuring a striped image pattern with 19 µm pitch by a complementary metal-oxide semiconductor (CMOS) image sensor without an LCP film. FIG. 9*b* is a view illustrating an image obtained by measuring after the same pattern as shown in FIG. 9*a* is attached to a CMOS image sensor of a 25 µm LCP film to which an optical window generation process is not applied.

Referring to FIGS. 9*a* and 9*b*, in the case of the LCP film having a thickness of 25 µm, it may be checked that a striped pattern is hardly distinguished.

Figure 9C:
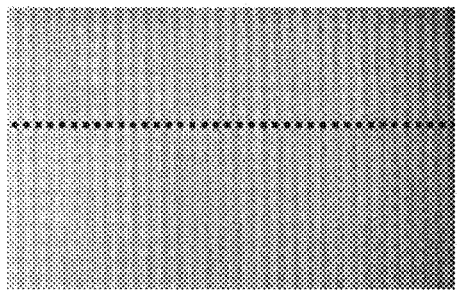
FIG. 9c is an image obtained by measuring when silicon having a flat surface during an optical window generation process and a 15 μm thick liquid crystal polymer film generated after the optical window generation process are attached to a CMOS image sensor.

FIG. 9*c* is an image obtained by measuring when silicon having a flat surface during an optical window generation process and a 15 µm thick liquid crystal polymer film generated after the optical window generation process are attached to a CMOS image sensor according to embodiments of the present invention. Unlike FIG. 9*b*, it is possible to definitely confirm that a striped pattern is definitely distinguished.

Figure 9D:
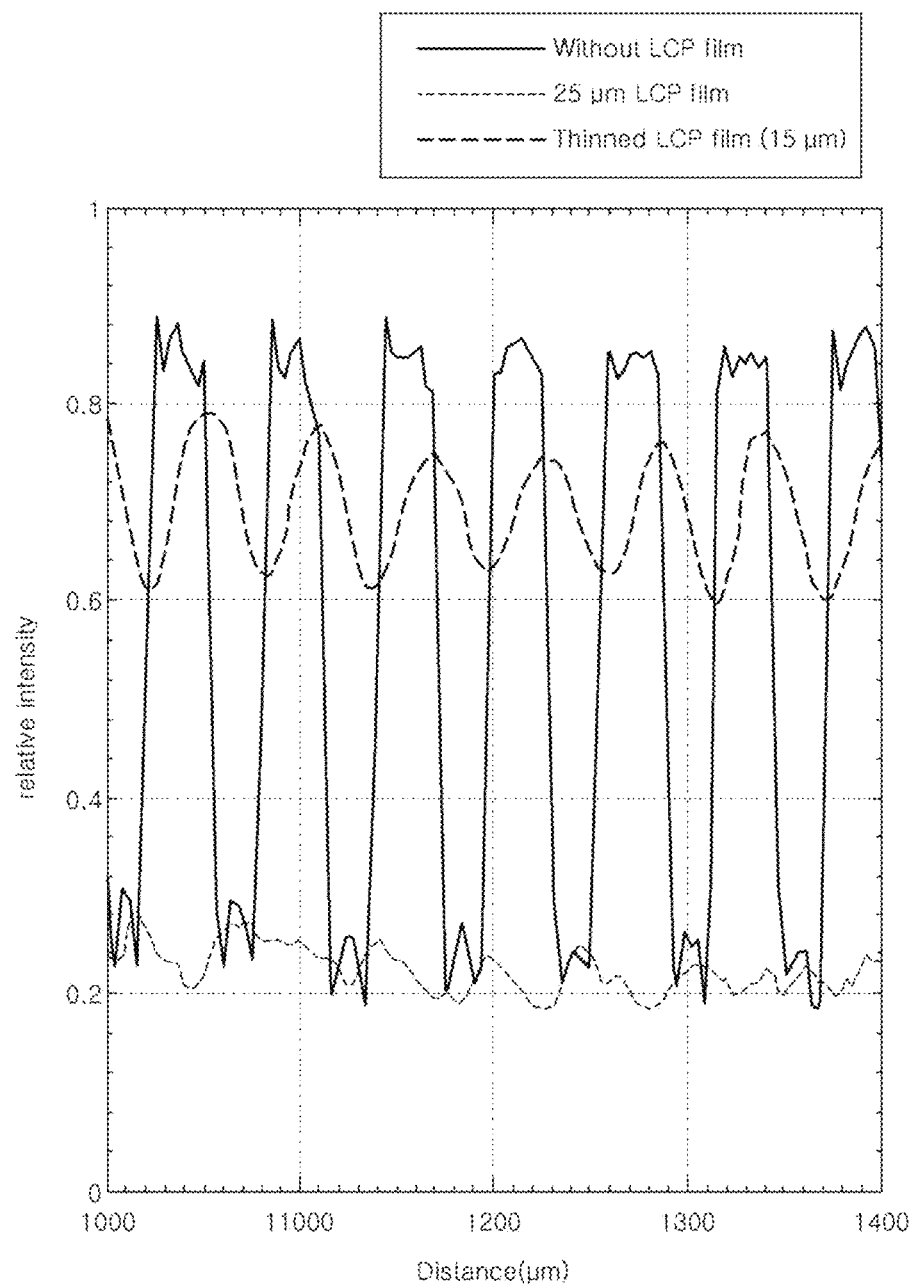
FIG. 9d is a graph illustrating information (relative intensity) of a pixel corresponding to a horizontal line of the images of FIGS. 9a to 9c.

Also, FIG. 9*d* is a graph illustrating information (relative intensity) of a pixel corresponding to a horizontal line of the images of FIGS. 9*a* to 9*c*.

Figure 10:
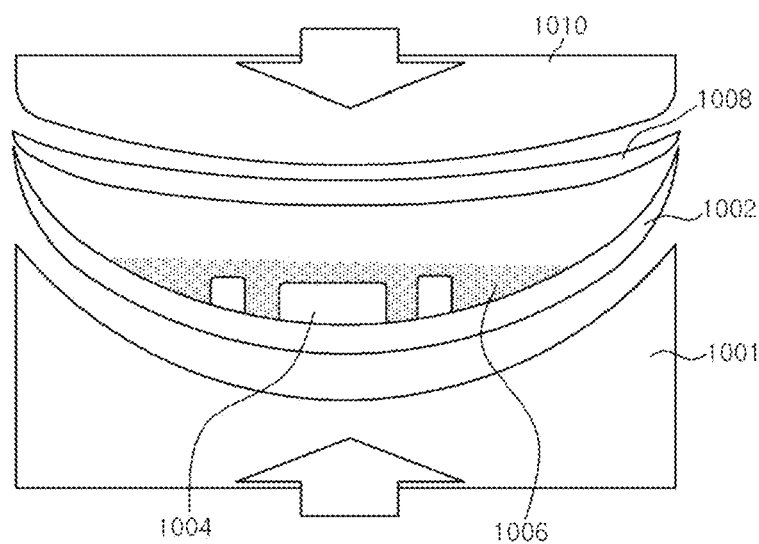
FIG. 10 is a cross-sectional view illustrating a process of manufacturing a curved type sealed package according to embodiments of the present invention.

FIG. 10 is a cross-sectional view illustrating a process of manufacturing a curved type sealed package according to embodiments of the present invention. Here, the curved type sealed package may refer to, for example, a package and the like applied to an eyeball-attached artificial retina system.

Referring to FIG. 10, a curved type LCP substrate 1002 is prepared and at least one electronic component 1004 is mounted on (assembled with) a curved area of the prepared curved type LCP substrate 1002.

Next, to completely embed the electronic component 1004, the curved area of the curved type LCP substrate 1002 is filled with LCP powder 1006. Here, the powder may be powder formed by mechanically grinding LCP pellets or film.

Here, filling the curved area with the LCP powder 1006 is intended to suppress an external mechanical shock and an internal moisture condensation possibility after packaging.

Once again, a concave LCP cover layer 1008 is aligned at a target position on the curved type LCP substrate 1002 with the curved area filled with the LCP powder 1006 and a packaging process such as thermocompression and the like is performed using a curved type lower press jig 1001 opposite to a curved surface and a concave type upper press jig 1010 opposite to a concave surface, thereby manufacturing a curved type sealed package in which the curved type LCP substrate 1002 and the concave type LCP cover layer 1008 are packaged (compressed).

Meanwhile, although an example in which the present invention is applied to an LCP-based neural implant has been described, the present invention is not limited thereto and may be identically applied to the field of microelectromechanical systems (MEMS) and the like.

Although the technical concept of the present invention has been exemplarily described above, one of ordinary skill in the art may easily understand that various substitutions, modifications, alterations and the like can be made without departing from the essential features of the present invention. That is, the embodiments of the present invention described above are not intended to limit the technical concept of the present invention but to explain the same. The scope of the technical concept of the present invention is not limited thereto.

Accordingly, it will be understood that the scope of the present invention should be defined by the following claims and all the technical concepts within an equivalent scope thereof should be included in the scope of the present invention.

The invention claimed is:

1. A method of manufacturing a package for an LCP-based neural implant, comprising:
    mounting an electronic component at a certain position on an electronic board;
    manufacturing a component structure by stacking an intermediate substrate having a cavity that accommodates the electronic component on the electronic board;
    aligning the component structure at a certain position on an LCP substrate;
    manufacturing a package by aligning and pressurizing an LCP cover layer on the component structure; and
    filling the cavity with LCP powder after the manufacturing of the component structure.

2. The method of claim 1, wherein the intermediate substrate is formed of an LCP film in a multilayer structure.

3. The method of claim 1, wherein the cavity is formed through a laser etching process.

4. The method of claim 1, further comprising, before the aligning of the LCP cover layer, forming an optical window at a certain position on the LCP cover layer.

5. The method of claim 4, wherein the optical window is formed through a selective pressurizing process using a mold having flatness.

6. The method of claim 4, wherein the optical window is formed through a laser etching process.

7. The method of claim 4, wherein the optical window is formed through a plasma etching process.

\* \* \* \* \*